United States Patent [19]

Morse et al.

[11] Patent Number: 4,774,354

[45] Date of Patent: Sep. 27, 1988

[54] HYDROBORATE COMPOUNDS

[75] Inventors: Karen W. Morse, Providence; John L. Peters, Logan, both of Utah

[73] Assignee: Utah State University Foundation, Logan, Utah

[21] Appl. No.: 900,760

[22] Filed: Aug. 27, 1986

Related U.S. Application Data

[62] Division of Ser. No. 721,298, Apr. 9, 1985.

[51] Int. Cl.$^4$ ................. C07C 121/16; C07C 121/66
[52] U.S. Cl. .................................... 558/384; 260/690
[58] Field of Search ......................................... 558/384

[56] References Cited

Primary Examiner—Anton H. Sutto
Attorney, Agent, or Firm—Workman, Nydegger & Jensen

[57] ABSTRACT

The present invention relates to novel organocyanohydroborate compounds which may be employed as reducing agents. For example, organocyanohydroborates having the following general formula are contemplated:

$$M^+BH_3CR_1R_2CN^-$$

In this formula, $R_1$ and $R_2$ may be, for example, H, $CH_3$, or $C_6H_5$, or may be represented jointly, for example by $C_5H_{10}$, while $M^+$ is a cation which is capable of forming a salt. The organocyanohydroborate compounds of the present invention include a $-CR_1R_2-$ moiety between the $BH_3$ moiety and CN moiety to provide a new class of hydroborate reducing agents.

11 Claims, No Drawings

U.S. PATENT DOCUMENTS 4,658,051  7/1987  Morse et al. ......................... 558/384

OTHER PUBLICATIONS

Herbert C. Brown et al., "Hydroboration. III. The Reduction of Organic Compounds by Diborane, an Acid--Type Reducing Agent," 82, *Journal of the American Chemical Society*, 681-686 (1960).
Leo J. Malone et al., "The Preparation and Properties of the Boranocarbonates", 6, *Inorganic Chemistry*, 817-822, No. 4 (1967).
Leo J. Malone, "The Alcoholysis of Carbon Monoxide Borane," 7, *Inorganic Chemistry*, 1039-1040 (1968).
Toshio Satho et al., "Reduction of Organic Compounds with Sodium Borohydride-Transition Metal Salt Systems (1)-Reduction of Organic Nitrile, Nitro and Amide Compounds to Primary Amines," *Tetrahedron Letters*, 4555-4558, No. 52 (1969).
B. D. Hoewe et al., "The Aminolysis and Basic Hydrolysis of the O-Ethylboranocarbonate Ion", 10 *Inorganic Chemistry*, 930-933, No. 6 (1971).
Gordon W. Gribble et al., "Reactions of Sodium Borohydride in Acidic Media I. Reduction of Indoles and Alkylation of Aromatic Amines with Carboxylic Acids," 96, *Journal of the American Chemical Society*, 7812-7814, No. 25 (1974).
Clinton F. Lane, "Organic Synthesis via Organoboranes II-Selective Reductions Using Borane-Tetrahydrofuran Complex," 7, *Aldrichimica Acta*, 7-8 (1974).
Clinton F. Lane, "Ester Reductions with Super-Hydride," 7, *Aldrichimica Acta*, 32-33 (1974).
Paolo Marchini et al., "Sodium Borohydride-Carboxylic Acid Systems. Useful Reagents for the Alkylation of Amines," 40, *Journal of Organic Chemistry*, 3453-3456, No. 23 (1975).
Gordon Gribble et al., "Reactions of Sodium Borohydride in Acidic Media. Selective Reduction of Aldehydes with Sodium Triacetoxyborohydride," *Journal of the Chemical Society Chemical Communications*, 535-536 (1975).
Gordon W. Gribble et al., "Reactions of Sodium Borohydride in Acidic Media III. Reduction and Alkylation of Quinoline and Isoquinoline with Carboxylic Acids," *Synthesis*, 650-652 (1975).
Norihide Umino et al., "Sodium Acytoxyborohydride as New Reducing Agents. I. Reduction of Carboxamides to the Corresponding Amines," *Tetrahedron Letters*, 763-766, No. 10 (1976).
Norhide Umino et al., "Sodium Acytoxyborohydride as New Reducing Agents II. Reduction of Nitrites to the Corresponding Amines," *Tetrahedron Letters*, 2875-2876, No. 33 (1976).
Jerry C. Bommer et al., "$(MePh_2P)_3CuBH_4$): A Single M-H Bridged Tetrahydroborate," *Journal of the Chemical Society Chemical Communications*, 137-138 (1977).
S. Krishnamurthy et al., "Selective Reductions. 22. Facile Reduction of Alpha, Beta-Unsaturated Aldehydes and Ketones with 9-Borabicyclo (3.3.1) Nonane. A Remarkably Convenient Procedure for the Selective Conversion of Conjugated Aldehydes and Ketones to the Corresponding Allylic Alcohols in the Presence of Other Functional Groups," 42, *Journal of Organic Chemistry*, 1197-1201, No. 7 (1977).
Herbert C. Brown et al., "Selective Reductions. 23. Assymmetric Reduction of Representative Ketones with Diisopinocampheylborane of High Optical Purity," 42, *Journal of Organic Chemistry*, 2996-2999, No. 18 (1977).
Michael J. Haire, "Improved Reduction of Nitrimines to Nitramines Using Sodium Borohydride and Acetic Acid, " 42, *Journal of Organic Chemistry*, 3446-3447 (1977).
Herbert C. Brown et al., "Selective Reductions. 24. Acyloxyboranes in the Controlled Reaction of Carboxylic Acids with Borane-Tetrahydrofuran. Acyloxyboranes as Intermediates in the Fast Reduction of Carboxylic Acids by Borane-Tetrahydrofuran," 99, *Journal of the American Chemical Society*, 8218-8226 (1977).
Clinton F. Lane, "Selective Reductions Using Borane Complexes," 10, *Aldrichimica Acta*, 41-51, No. 3 (1977).
Herbert C. Brown et al., "Simple Synthesis of Monoisopinocampheylborane of High Optical Purity," 43, *Journal of Organic Chemistry*, 4395-4397 (1978).

(List continued on next page.)

OTHER PUBLICATIONS

G. W. J. Fleet et al., "Bis(Triphenylphosphine) Copper (I) Tetrahydroborate in the Reduction of Acid Chlorides to Aldehydes," *Tetrahedron Letters*, 1437–1440, No. 16 (1978).

Thomas N. Sorrell et al., "Metal Tetrahydroborate Complexes: Selective Reducing Agents for Organic Synthesis," *Tetrahedron Letters*, 2473 (1978).

Gordon W. Gribble et al., "Reactions of Sodium Borohydride in Acidic Media; Reduction of Diaryl Ketones in Trifluoroacetic Acid," *Synthesis*, 763–765 (1978).

Gordon W. Gribble et al., "Reactions of Sodium Borohydride in Acidic Media; VIII. N-Alkylation of Aliphatic Secondary Amines with Carboxylic Acids," *Synthesis*, 766–768 (1978).

J. C. Bommer et al., "Slowing of the Fluxional Process in a Diamagnetic Copper(I) Tetrahydroborate Complex," 17 *Inorganic Chemistry* 3708–3710 (1978).

Surendra U. Kulkarni et al., "2,6-Diboraadamantane, a Novel Structure with Unus Characteristics, via Cyclic Dihydroboration of 1,3,5,7-Cyclooctatetraene," 44 *Journal of Organic Chemistry* 1747–1749, No. 10 (1979).

S. Krishnamurthy et al., "Selective Reductions. 25. Remarkably Facile Reductive Opening of Cyclic Ethers by the Lithium Tri-tert-butoxyaluminohydride-Triethylborane Combination," 44 *Journal of Organic Chemistry* 3678–3682, No. 21 (1979).

Herbert C. Brown, "Hydride Reductions: A 40-year Revolution in Organic Chemistry," *Chemical & Engineering News* 24–29 (Mar. 5, 1979).

Herbert C. Brown et al., "Molecular Addition Compounds. 5. Interaction of N,N,N',N'-Tetramethylethylenediamine with Boron Trifluoride and Monoalkylboranes 18 *Inorganic Chemistry* 51–53 (1979).

Herbert C. Brown et al., "Molecular Addition Compounds. 6. Addition Compounds of Ethylenediamine with Boron Trifluoride and Dialkylboranes," 18 *Inorganic Chemistry*, 53–55 (1979).

Jerry C. Bommer et al., "Transition-Metal-(Carboxylato)trihydroborate Complexes Copper and Silver Triphenylphosphine Complexes of $H_3BCO_2R^-$ (R=H, $CH_3$, $C_2H_5$),"1 8 *Inorganic Chemistry* 531–538 (1979).

Herbert C. Brown et al. "Tetrahedron Report Number 64–Forty Years of Hydride Reductions," 35 *Tetrahedron Letters* 567–607 (1979).

G. W. J. Fleet et al., "Convenient Synthesis of Bis(Triphenylphosphine) Copper(I) Tetrahydroborate and Reduction of Acid Chlorides to Aldehydes," *Tetrahedron Letters*, 975–978, No. 11 (1979).

Gordon W. Gribble, "Sodium Borohydride in Carboxylic Acid Media-New Synthetic Methodology," 51 *Eastman Organic Chemical Bulletin* 1–6, No. 1 (1979).

Jerry C. Bommer et al., "Single Hydrogen-Boron Bridged Species: Tris-(methyldiphenylphosphine) Complexes of Silver(I) and Copper (I) Containing Tetrahydroborate and (Ethoxycarbonyl)trihydroborate," 19 *Inorganic Chemistry* 587–593 (1980).

Benjamin C. Hui, "Synthesis and Properties of Borohydride Derivatives", 19 *Inorganic Chemistry* 3185–3186 (1980).

Herbert C. Brown et al., "Selective Reductions. 26. Lithium Triethylborohydride as an Exceptionally Powerful and Selective Reducing Agent in Organic Synthesis; Exploration of the Reactions with Selected Organic Compounds Containing Representative Functional Groups," 45 *Journal of Organic Chemistry* 1–12, No. (1980).

Herbert C. Brown et al., "Molecular Addition Compounds. 8. $^{13}C$ and $^{11}B$ NMR Examination of B-Substituted Derivatives of 9–Borabicyclo(3.3.1)nonane and Their Pyridine Complexes," 45 *Journal of Organic Chemistry* 846–849 (1980).

S. Krishnamurthy et al., "Selective Reductions. 27. Reaction of Alkyl Halides with Representative Complex Metal Hydrides and Metal Hydrides; Comparison of Various Hydride Reducing Agents," 45 *Journal of Organic Chemistry* 849–856 (1980).

Robert O. Hutchins et al., "mu-Bis(Cyanotrihydroborato)Tetrakis(Triphenylphosphine) Dicopper(I); A New, Selective, pH Dependent Reducing Agent," *Tetrahedron Letters* 813–816 (1980).

G. W. J. Fleet, "Bis(Triphenylphosphine)Copper(I) Tetrahydroborate in the Reduction of P-Toluenesulphonylhydrazones and 2, 4, 6-Triisopropylbenzenesulphonyl Hydrazones (Trisyl Hydrazones) to Alkanes," 21 *Tetrahedron Letters* 4031–4034 (1980).

Herbert C. Brown et al., "Addition Compounds of Alkali Metal Hydrides. 20. Reaction of Representative Mono- and Dialkylboranes with Saline Hydrides to Form the Corresponding Alkylborohydrides," 46 *Journal of Organic Chemistry* 2712–2717 (1981).

Herbert C. Brown et al., "Tetrahedron Report No. 116–"Asymmetric Syntheses Via Chiral Organoborane Reagents," 37 *Tetrahedron* 3547–3587 (1981).

Yoshinori Yamamoto et al., "Reaction of Allylic Boron and Aluminum "Ate" Complexes with Organic Halides and Carbonyl Compounds; Trialkylboranes as Regio-, Stereo-, and Chemoselective Control Elements," 103 *Journal of the American Chemical Society* 1969–1975 (1981).

Fusao Takusagawa et al., "Neutron and X-ray Diffraction Studies of Tris-(methyldiphenylphosphine)(tetrahydroborato(1))copper, $Cu(P(C_6H_5)_2CH_3)_3(BH_4)$; The First Accurate Characterization of an Unsupported Metal-Hydrogen-Boron Bridge Bond," 103 *Journal of the American Chemical Society* 5165–5171 (1981).

Jerry C. Bommer et al.,"Temperatures-Dependent Phosphite Complex Equilibria Observable with NMR and IR Techniques," 20 *Inorganic Chemistry* 1731–1734 (1981).

Herbert C. Brown et al., "New Powerful Catalysts for the Reduction of Esters by Lithium Borohydride," 47 *Journal of Organic Chemistry* 1604–1606 (1982).

Herbert C. Brown et al., "Selective Reductions. 29. A Simple Technique to Achieve an Enhanced Rate of Reduction of Representative Organic Compounds by Borane-Dimethyl Sulfide," 47 *Journal of Organic Chemistry* 3153–3163 (1982).

(List continued on next page.)

OTHER PUBLICATIONS

Herbert C. Brown et al., "Selective Reductions. 30. Effect of Cation and Solvent on the Reactivity of Saline Borohydrides for Reduction of Carboxylic Esters; Improved Procedures for the Conversion of Esters to Alcohols by Metal Borohydrides," 47 *Journal of Organic Chemistry* 4702–4708 (1982).

S. Krishnamurthy et al., "Selective Reductions. 31. Lithium Triethylborohydride as an Exceptionally Powerful Nucleophile; A New and Remarkably Rapid Methodology for the Hydrogenolysis of Alkyl Halides under Mild Conditions," 48 *Journal of Organic Chemistry* 3085–3091 (1983).

Herbert C. Brown et al., "Selective Reductions. 32. Structural Effects on the Reduction of Epoxides by Lithium Triethylborohydride; A Kinetic Study," 48 *Journal of Organic Chemistry* 3091–3096 (1983).

Herbert C. Brown et al., "Organoboranes. 31. A Simple Preparation of Boronic Esters from Organolithium Reagents and Selected Trialkoxyboranes," 2 *Organometallics* 1316–1319 (1983).

Werner Biffar et al., "Chemistry of Boron. 130. The Reaction of Organolithium Compounds with Borane Donors; Preparation and Isolation of Lithium Monoorganotrihydroborates," 2 *Organometallics* 579–585 (1983).

J. C. Bommer et al., "Singly Bridged Hydroborates: Fluxional Character in $((MeO)_3P)_2CuBH_4$ and a Calculation of Delta $\bar{G}$ for the Process,38 74 *Inorganica Chimica Acta* 25–27 (1983).

Bernard F. Spielvogel et al., "Predictive Schemes for the Reactivity of Borane Carbonyl and the Stability of Carbonyltrihydroborate Anions, $BH_3C(O)X^-$," 2 *Polyhedron* 1345–1352, No. 12 (1983).

Herbert C. Brown et al., "Selective Reductions. 33. Potassium Triisopropoxyborohydride as a Selective Reducing Agent in Organic Synthesis; Reaction with Selected Organic Compounds Containing Representative Functional Groups," 49 *Journal of Organic Chemistry* 885–892 (1984).

Paul G. Egan, et al., "$(Ph_2MeP)_3Cu(NC)_2(BH_2)$ and $P^3Cu(NC)_2BH_2(P^3=1,1,1$-Tris((diphenylphosphino)methyl)ethane): The First Metal Complexes of Dicyanodihydroborate," 23 *Inorganic Chemistry* 2203 (1984).

Herbert C. Brown et al., "Molecular Addition Compounds. 9. Effect of Structure on the Reactivities of Representative Borane-Amine Complexes in Typical Reactions Such as Hydrolysis, Hydroboration, and Reduction," 23 *Inorganic Chemistry* 2746–2753 (1984).

Herbert C. Brown et al., "Addition Compounds of Alkali-Metal Hydrides. 24. A General Method for Preparation of Potassium Trialkoxyborohydrides; A New Class of Reducing Agents," 23 *Inorganic Chemistry* 2929–2931 (1984).

Bakthan Singaram et al., "Addition Compounds of Alkali-Metal Hydrides. 25. Rapid Reaction of Boronic Esters and Acids with Lithium Aluminum Hydride; A Novel and Quantitative Synthesis of Lithium Monoorganylborohydrides," 3 *Organometallics* 774–777 (1984).

Bakthan Singaram et al., "Addition Compounds of Alkali-Metal Hydrides. 26. Facile Reaction of Borinic Esters with Lithium Monoethoxyaluminohydride to form Lithium Dialkylborohydrides," 3 *Organomettallics* 1520–1523 (1984).

Stephen Stinson, "Method Synthesizes Chiral Boranes In 100% Optical Purity," 62 Chemical & Engineering News 28–29 (Mar. 26, 1984).

Herbert C. Brown et al., "Chiral Synthesis via Organoboranes. 1. A Simple Procedure to Achieve Products of Essentially 100% Optical Purity in Hydroboration of Alkenes with Monoisopinocampheylborane; Synthesis of Boronic Esters and Derived Products of Very High Enantiomeric Purities," 106 *Journal of the American Chemistry Society* 1797–1800 (1984).

Herbert C. Brown et al., "Chiral Synthesis via Organoboranes. 2. Rapid Reaction of Boronic Esters of Very High Optical Purity with Lithium Aluminum Hydride; Facile Reaction of Essentially Optically Pure Borinic Esters with Lithium Monoethoxyaluminohydride; A Novel and Quantitative Synthesis of Lithium Monoalkyl- and Dialkylborohydrides of Essentially 100% Optical Purity," 107 *Journal of the American Chemical Society* 460–464 (1985).

HYDROBORATE COMPOUNDS

This is a division of application Ser. No. 721,298 filed Apr. 9, 1985.

BACKGROUND

1. The Field of the Invention

The present invention relates to a new class of hydroborate compounds, and to the use of these compounds as reducing agents. In particular, the present invention relates to a family of organocyanohydroborates which may be used as chemically selective reducing agents in a variety of important chemical reactions.

2. The Prior Art

Hydroborate compounds are known to be useful as reducing agents in a variety of important chemical reactions and are important compounds in modern organic synthesis. Additionally, hydroborates may be coordinated to a metal so as to provide certain reducing and catalytic properties. However, the applications of known hydroborate compounds are unfortunately often limited because of the scope of their reducing properties.

Examples of hydroborate compounds used in the prior art include: (1) trialkylhydroborates, (2) cyanotrihydroborates, (3) acetoxyhydroborates, (4) carboxylatotrihydroborates, and (5) monoalkyltrihydroborates. The trialkylhydroborates include trisubstituted hydroborate anions of the following general formula: $R_3BH^-$. The trialkylhydroborates are generally considered strong reducing agents.

The cyanotrihydroborate compounds include an anion having the general formula: $BH_3CN^-$. In contrast to the trialkylhydroborates, the cyanotrihydroborate compounds are generally considered to be mild reducing agents. Thus, there is a relatively large gap between the reducing potentials of the cyanotrihydroborates and the trialkylhydroborates.

In connection with the milder reducing potential, the addition of the cyano (CN) moiety directly to the boron in the cyanotrihydroborate compounds has resulted in much more useful reagents for the selective reduction of some organic functional groups, particularly in view of its stability at low pH. The electron-withdrawing effect of the cyano group is thought to be responsible for the broader applicability of the cyanotrihydroborate compounds at low pH. Thus, the cyanotrihydroborate compounds have provided for some reducing versatility not experienced with other hydroborate reducing compounds.

Indeed, cyanotrihydroborates have found utility in the following exemplary areas: trapping carbonium ions, direct synthesis of $NaBD_3CN$ and $NaBH_3CN$-t, curing a liquid nitrile polymer and a polymer made from an aliphatic mercaptan and a conjugated diene, reductive bleaching of groundwood pulp, sulfate pulp, and chemi-ground wood pulp without corrosion of the equipment, fluorescent labeling of saccharides, the reductive amination of proteins, synthetic studies on glycocinnamoylspermidines, studies producing alpha-2 antagonism, the reduction of rhodopsin, the regioselective reduction of phenylthiazines, the reductive methylation of proteins, the study of the synthesis and dopamine receptor binding of exo- and endo-2-amine-6,7-dihydroxybenzonorbornene, and the reductive ring opening of carbohydrate benzylidene acetals.

The acetoxyhydroborates contain an anion having the general formula: $H_{3-x}B(CO_2CCR_3)_x^-$; the carboxylatotrihydroborates incorporate an anion having the general formula: $H_3BCO_2^{2-}$ or $H_3BCO_2R^-$; and the monoalkyltrihydroborates contain an anion having the general formula: $RBH_3^-$. Unfortunately, each of these anions is typically difficult to make and difficult to isolate in a pure form. Thus, the prior art acetoxyhydroborates, carboxylatotrihydroborates, and monoalkyltrihydroborates, have not provided practical reducing agents because of the difficulty in manufacturing and purifying these hydroborate compounds.

In view of the advantages and diversity exhibited by the prior art cyanotrihydroborate compounds, it would be a significant advancement in the art to further diversify the reducing capabilities of such cyanotrihydroborate compounds so as to span the gap of reducing potential between the prior art cyanotrihydroborates and trialkylhydroborates. Additionally, it would be an advancement to provide cyanotrihydroborate compounds which exhibit a greater degree of control over the extent and selectivity of the chemical reduction accomplished.

From the foregoing, it will be appreciated that what is needed in the art are hydroborate compounds which have a wider versatility of reducing capability and which have a reducing capability between the strong and mild reducing hydroborate compounds presently known in the art. It would be another significant advancement in the art to provide a class of hydroborate compounds which are relatively easy to make and to isolate in pure form.

Moreover, it would be another significant advancement in the art to provide a new class of hydroborate compounds which incorporate a cyano moiety and other substituent groups which provide for a class of hydroborate compounds having not only all of the advantages of the prior art cyanotrihydroborate compounds, but also greater versatility and wider application as reducing agents.

Such hydroborate compounds and methods for manufacturing and using such compounds as reducing agents are disclosed and claimed herein.

BRIEF SUMMARY AND OBJECTS OF THE INVENTION

The present invention relates to novel reducing agents which are organocyanohydroborates. These novel organocyanohydroborates have the following general formula:

$$M^+BH_3CR_1R_2CN^- \qquad (1)$$

In Formula 1 above, $R_1$ is either H, $CH_3$, or $C_6H_5$. Likewise, $R_2$ is either H, $CH_3$, or $C_6H_5$. Also, $R_1$ and $R_2$ may be represented together by $C_5H_{10}$ so as to form a cyclic hydrocarbon. Further, $M^+$ is a cation having, for example, a charge of $1+$.

The $M^+$ cation in the above-identified formula may be virtually any cation which forms a salt with the $BH_3CR_1R_2CN^-$ anion. For example, lithium ($Li^+$) and tetraphenylphosphonium $(C_6H_5)_4P^+$ have been found suitable cations for purposes of $M^+$ in Formula 1.

The organocyanohydroborate compounds of the present invention provide a wide variety of reducing capability by varying the substituent groups $R_1$ and $R_2$ in the above-indicated formula. Moreover, the present invention also relates to various derivatives of the above-identified compounds, such as the dioxane adducts and amine derivatives. Also, the present invention relates to methods for manufacturing and using such organocyanohydroborate compounds as reducing agents, and in particular, as selective reducing agents.

It is, therefore, an object of the present invention to provide novel organocyanohydroborate compounds and methods for readily and easily producing the same.

A further object of the present invention is to provide a new class of hydroborate compounds which have a wide range of reducing capabilities, and which have versatile reducing capabilities not heretofore known in the art.

Still another object of the present invention is to provide a class of hydroborate compounds which are relatively easy to make and to isolate in pure form.

Yet another object of the present invention is to provide a class of hyroborate compounds which provide for selective chemical reduction of different chemical species, and which have wide application in the areas of organic synthesis.

These and other objects and features of the present invention will become more fully apparent from the following description and appended claims.

DETAILED DESCRIPTION OF THE PREFERRED EMBODIMENTS

The present invention relates to organocyanohydroborate compounds having an anion of the general formula: $BH_3CR_1R_2CN^-$. When combined with a cation to form an ionic salt, these novel hydroborates have the general formula: $M^+BH_3CR_1R_2CN^-$.

The organocyanohydroborate compounds of the present invention may be used in traditional organic syntheses wherein, for example, it is desired to transform a carbonyl group, an aldehyde, or a carboxylic acid group into an alcohol group. Additionally, as will be explained in more detail hereinafter, the compounds of the present invention may also be used to provide for selective reduction of one or more of such organic functional groups.

The novel organocyanohydroborate compounds within the scope of the present invention are further represented in Formulas 2A and 2B below.

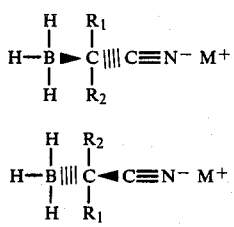

FORMULA 2A

FORMULA 2B

It will be appreciated that Formulas 2A and 2B above merely represent the two different enantiomers which are possible from the general formula $M^+BH_3CR_1R_2CN^-$. In this regard, it will be appreciated that all steroisomers of the formulas set forth herein with respect to the compounds of the present invention are within the scope of the present invention.

In the above-identified Formulas 2A and 2B, it is anticipated that $R_1$ and $R_2$ may be any substituent groups which will form a stable organocyanohydroborate compound. To date, compounds have been formed where $R_1$ and $R_2$ are represented by various combinations of H, $CH_3$, and $C_6H_5$, and wherein $R_1$ and $R_2$ are jointly represented by $C_5H_{10}$ in a cyclic hydrocarbon. Additionally, some deuterated substitutions of these compounds have been prepared.

It will be further appreciated that substituent groups, having, for example, halogen, nitro, or heterocyclic ring substitutions, as well as other substituent groups, besides hydrogen, methyl, and phenyl groups may also be used in the place of $R_1$ and $R_2$, and that the present invention is not restricted to those particular R groups only. For example, it is anticipated that $C_2H_5$, $C_3H_7$, $C_4H_9$, $C_5H_{11}$, $C_6H_{13}$, etc., and substitutions thereof, may be used for $R_1$ and $R_2$ in the present invention. Hence, it will be understood that virtually any R groups which will form a stable organocyanohydroborate compound when substituted for $R_1$ and $R_2$ are within the scope of the present invention.

Similarly, the $M^{30}$ cation in each of Formulas 2A and 2B represents the cations (having, for example, a 1+ charge) which may be associated with the anions of the present invention. Thus, $M^+$ may be virtually any cation which is capable of forming a salt with the anions of the present invention to form organocyanohydroborates. By way of example only, it has been found that lithium ($Li^+$) and tetraphenylphosphonium $(C_6H_5)_4P^+$) may be used as suitable cations in forming organocyanohydroborates within the scope of the present invention.

However, once again, it will be appreciated that, as far as the $M^+$ cation is concerned, the present invention is not limited to the aforementioned cations only, but that virtually any suitable cation may be substituted for $M^+$ within the scope of the present invention. In this regard, cations having a charge larger than 1+ (e.g., 2+, 3+, 4+) may be used to form hydroborate salts in accordance with the present invention by associating the appropriate number of hydroborate anions therewith.

One presently preferred method for the preparation of the organocyanohydroborate compounds within the scope of the present invention involves a synthesis represented in Equations I and II below:

EQUATION I

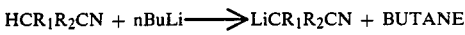

$HCR_1R_2CN + nBuLi \longrightarrow LiCR_1R_2CN + BUTANE$

EQUATION II

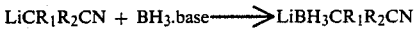

$LiCR_1R_2CN + BH_3 \cdot base \longrightarrow LiBH_3CR_1R_2CN$

For purposes of illustration, lithium ($Li^+$) is used in the examples of Equations I and II as the cation component of the organocyanohydroborate salts formed. Obviously, other cation-forming chemical species could be substituted for lithium in Equations I and II above, for example, cations of the alkali and alkaline earth elements.

It has been discovered that, in order to optimize the recovery and purity of the organocyanohydroborate compound produced as a result of Equations I and II above, the reaction conditions must be carefully controlled. Otherwise, by-products resulting from hydride transfer, such as lithium borohydride ($LiBH_4$) in the example of Equations I and II, may be produced.

In order to minimize such undesired by-products, it has been found that the temperature of the reaction of Equation I should be preferably kept within the range of from about $-60°$ C. to about $-80°$ C., and that the temperature of the reaction of Equation II should also be preferably kept within the range of from about about −60° C. to about −80° C. While it will be recognized that temperatures lower than −80° C. may be used for the reactions of Equations I and II, the reaction rate would be undesirably slower. Moreover, although temperatures higher than −60° C. may be used, undesirable polymerization reactions tend to occur at these higher temperatures. Hence, it has been found that the presently preferred temperature range for the reactions of Equations I and II is from about −60° C. to about −80° C.

Further, the addition modes and reaction ratios become important in optimizing the purity of the particular organocyanohydroborate produced. For example, it has been found that optimum purity of product is achieved when the molar ratio of n-butyllithium to $BH_3$ is within the range of about 2–3:1, and the molar ratio of the $HCR_1R_2CN$ to $BH_3$ is within the range of about 5–8:1.

In the presently most preferred embodiment, it has been found that optimum purity of the $MBH_3CR_1R_2CN$ product is achieved when the molar ratio of n-butyllithium to $BH_3$ is about 2.5 to 1 and the molar ratio of $HCR_1R_2CN$ to $BH_3$ is about 6.5 to 1. The use of molar ratios lesser or greater than those set forth herein tend to provide larger amounts of by-products, such as $LiBH_4$ in the example of Equations I and II. Indeed, significant deviation from these molar ratios may result in $LiBH_4$ being the major product.

In one preferred embodiment, the reactions of Equations I and II are carried out in tandem, that is to say, the reaction of Equation I is carried out and the product of this reaction is immediately combined with the $BH_3$-base of Equation II. This may be accomplished by adding the $BH_3$-base to the product mixture of Equation I or by adding the product mixture of Equation I to a solution of $BH_3$-base (the base being, for example, tetrahydrofuran). Likewise, the $BH_3$-base may be added directly to the reaction vessel within which Equation I was carried out. Hence, it will be appreciated that the reactions of Equations I and II may be carried out in separate vessels or together in the same vessel as desired.

As a further note of interest, it has been discovered that the relative concentrations of the reactants in each of Equations I and II do not presently appear to significantly affect the purity of product obtained. Thus, the reactions of Equations I and II may be carried out in either concentrated or dilute solutions of the reactants without significantly affecting the yield or purity of the organocyanohydroborate produced. Hence, it will be recognized that the temperature and molar ratios of the reactants are the most critical parameters to control in obtaining purity of product in accordance with the present invention.

Another important factor in obtaining purity of product in accordance with the present invention is to carefully dry all of the equipment and solvents used. For example, by heating the glassware, assembling the glassware while hot, and allowing the glassware to cool under a nitrogen atmosphere in the assembled position, a relatively dry system is provided. Further, the water in the reagents and solvents used should be removed, and any conventional techniques for so drying the reagents and solvents may be employed for this purpose. Several examples of reagent drying methods are given in the examples set forth hereinafter.

Importantly, it should be further pointed out that the above-described method for obtaining a high yield and high purity organocyanohydroborate compound may also be used to obtain high yields and high purity in the production of hydroborate compounds known in the prior art. Hence, it will be appreciated that the method of the present invention for providing pure hydroborate compounds may be applied to virtually any prior art hydroborate compound so as to provide a relatively pure product.

When applying the purification methods of the present invention to prior art cyanohydroborate compounds, for example, the temperature ranges and molar ratios of reactants are substantially the same as those used in producing the novel organocyanohydroborate compounds of the present invention. Hence, the presently preferred temperature range for producing relatively pure cyanohydroborate compounds of the prior art using the methods of the present invention is from about −60° C. to about −80° C. Similarly, the presently preferred molar ratio of the derivative acetonitrile to the $BH_3$ is about 5–8:1, while the presently preferred molar ratio of the n-butyl metal compound to the $BH_3$ is about 2–3:1, with the presently most preferred ratios being 6.5 to 1 and 2.5 to 1, respectively.

As seen in Equations I and II, the derivative acetonitrile, which is a lower alkyl cyano compound, is reacted with the n-butyllithium base. However, it should be mentioned that virtually any base having a $pK_a$ greater than that of the lower alkyl cyano compound (estimated to be just under 25) may be used for purposes of the present invention. Thus, any base having a $pK_a$ of about 25 or greater may be used for this purpose. For example, other lower alkyl metallic bases such as methyl sodium could be used as the base in Equation I. The alkyl cyano salt formed as a result of Equation I is then of course reacted with the $BH_3$ to form the particular cyanohydroborate compound of interest.

Another method which may be used in the preparation of organocyanohydroborate compounds within the scope of the present invention when a cation such as sodium ($Na^+$) is used involves Equation III below:

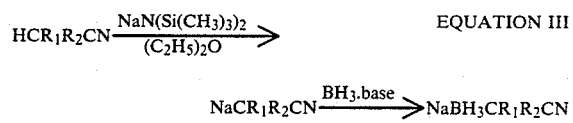

EQUATION III $$NaCR_1R_2CN \xrightarrow{BH_3 \cdot base} NaBH_3CR_1R_2CN$$

For purposes of illustration, sodium ($Na^+$) is used in the example of Equation III as the cation component of the organocyanohydroborate salt formed. Again, other cation-forming chemical species may be substituted for sodium in Equation III above.

Yet another method which may be used in the preparation of organocyanohydroborate compounds within the scope of the present invention when a cation such as cesium ($Cs^+$) is used involves Equation IV below:

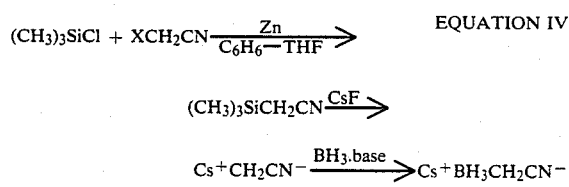

EQUATION IV $$(CH_3)_3SiCH_2CN \xrightarrow{CsF}$$

$$Cs^+CH_2CN^- \xrightarrow{BH_3 \cdot base} Cs^+BH_3CH_2CN^-$$

For purposes of illustration, cesium ($Cs^+$) is used in the example of Equation IV as the cation component of the organocyanohydroborate salt formed. Again, other cation-forming chemical species may be substituted for cesium in Equation IV above.

It will be further appreciated that there are many cation exchange techniques which are known in the art and which may be used so as to substitute the cation component M+ for another cation component M+ in the organocyanohydroborate compounds of the present invention. For example, metathesis reactions involving insoluble salt precipitates may be employed to provide such a cation exchange.

Also within the scope of the present invention are various derivatives of the organocyanohydroborate compounds such as those set forth in Formulas 2A and 2B above. For example, certain dioxane adducts and amine derivatives of these compounds have also been made and isolated. In this regard, tetraphenylphosphonium salts and the dioxane adducts of the lithium salts where $R_1=H$ and $R_2=H$ have both been isolated and appear relatively stable in water at a pH of about 5.5 and in air with only some decomposition being observed (an estimated 18% decomposition) after about 24 hours.

The general formula for the dioxane derivatives of the organocyanohydroborate compounds of the present invention is given in Formula 3 below:

FORMULA 3

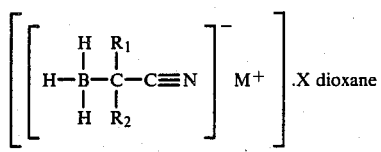

In Formula 3 above, X represents the average number of dioxane molecules which are associated with one molecule of the organocyanohydroborate compound. Experimentation done to date suggests that the value of X may be somewhere around 0.2. However, further studies will be conducted to more precisely determine the value of X. Further, it will be appreciated that as with Formulas 2A and 2B above, both enantiomers of the dioxane derivatives may be produced, and both are considered to be included in Formula 3 above.

One presently preferred method for preparing the dioxane derivatives of the organocyanohydroborate compounds of the present invention is as follows. First, the organocyanohydroborate compound produced in accordance with Formulas 2A and 2B is combined with enough 1,4-dioxane to dissolve the compound. Typically, about 35 milliliters of 1,4-dioxane is sufficient to dissolve about 17 millimoles of the organocyanohydroborate compound. The solution is then allowed to stand for a period of from about 45 minutes to about 60 minutes, during which time a white precipitate forms. The white precipitate, the dioxane derivative, may then be isolated by any standard technique, for example, by vacuum filtration.

The general formula for the amine derivatives of the organocyanohydroborate compounds of the present invention is given in Formula 4 below:

FORMULA 4

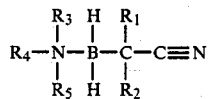

The amine derivatives of the organocyanohydroborate compounds of the present invention may be prepared in accordance with the reaction set forth in Equation V below.

EQUATION V

As seen in Equation V above, the amine derivatives of the organocyanohydroborate compounds of the present invention may be prepared by reacting the organocyanohydroborate compound with the hydrochloride salt or other acid salt of the amine compound to be added. This reaction is typically conducted at a temperature within the range of from about 25° C. to about 50° C. for a period of about 10 hours to about 30 hours.

Amine-organocyanoborane compounds which have been produced within the scope of the present invention include $(CH_3)_3NBH_2CHC_6H_5CN$, $(CH_3)_3NBH_2C(CH_3)_2CN$ and $(CH_3)_3NBH_2CH_2CN$, as will be discussed in further detail in Examples 32-34 below. However, it is anticipated that a variety of other amine-organocyanoborane compounds will be capable of production via the present invention. Additionally, as with the other organocyanohydroborate compounds of the present invention, the amine-organocyanoborane compounds serve to provide reducing agents for such basic organic functional groups as carbonyls, aldehydes, or carboxylic acids.

Another reason that the amine-organocyanoborane compounds of the present invention are of particular interest and importance is that presently known amine-cyanoboranes have shown utility as anti-arthritic, anti-tumor, anti-inflammatory, hypolipidemic, and hypocholesteremic agents. The amine-organocyanoborane compounds of the present invention are also anticipated to show similar biological activity.

Another class of compounds which may be produced within the scope of the present invention are the amine-organocarboxyborane compounds. These compounds may be produced by hydrolyzing the cyano group of the amine-organocyanoborane compounds discussed hereinabove. Such a hydrolysis reaction proceeds in either the presence of an acid (for example, sulfuric acid or hydrochloric acid) or a base (for example, sodium hydroxide) as indicated in Equation VI below.

EQUATION VI

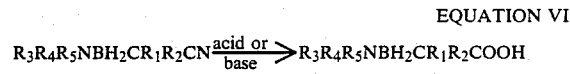

These amine-organocarboxyboranes, which are boron analogs of beta-amino acids, may well have clinical application as anti-arthritic, anti-inflammatory, and/or anti-tumor agents, as well as agents for the treatment of atherosclerosis. Additionally, as with the other organocyanohydroborate compounds of the present invention, the amine-organocarboxyborane compounds serve to provide reducing agents for such basic organic functional groups as carbonyls, aldehydes, or carboxylic acids.

Additionally, the organocyanohydroborate compounds of the present invention and the derivatives discussed herein are also capable of forming metal complexes in similar fashion as hydroborate compounds known in the prior art. For example, copper(I) complexes of the organocyanohydroborate compounds of the present invention can be prepared. An example of one method for producing such a copper(I) complex is given in Equation VII below. (In Equation VII, "L" represents any one of a number of various ligands which may be associated with the copper atom, for example, $(C_6H_5)_3P$, $(C_6H_5)_2CH_3P$, $(C_6H_5)(CH_3)_2P$, and $H_2PCH_2CH_2PH_2$.)

EQUATION VII $$L_3CuCl + BH_3CR_1R_2CN \longrightarrow L_{3-x}Cu(BH_3CR_1R_2CN)_x$$

In addition to the aforementioned derivatives, the organocyanohydroborate compounds of the present invention may also be used to synthesize a new class of boron and nitrogen-containing polymers. One proposed reaction mechanism for forming such polymers is given in Equation VIII below.

EQUATION VIII $$M^+BH_3CR_1R_2CN^- + HCl \xrightarrow[\text{anhydrous HCl}]{(C_2H_5)_2O}$$

$$(BH_2CR_1R_2CN)_n + H_2 + M^+ + Cl^-$$

Somewhat similar to the $(BH_2CN)_n$ polymers formed in the prior art, $(BH_2CR_1R_2CN)_n$ polymers may also be formed in accordance with the present invention. Indeed, the $(BH_2CR_1R_2CN)_n$ polymers of the present invention may be more stable than the $(BH_2CN)_n$ prior art polymers, due to the insertion of the $-CR_1R_2-$ moiety between the $BH_2$ and CN moieties in the polymers of the present invention.

As discussed herein, the prior art trailkylhydroborates provide relatively strong reducing agents, while the prior art cyanotrihydroborates provide relatively mild reducing agents. Additionally, other prior art hydroborate compounds, such as the acetoxyhydroborates, the carboxylatotrihydroborates, and the monoalkyltrihydroborates, are difficult to make and to isolate in pure form. Thus, the present invention provides a substantial advancement in the art by providing a wide variety of readily preparable and purifiable, new hydroborate reducing agents having reducing capabilities between those of the trialkylhydroborates and the cyanotrihydroborates.

The insertion of the $-CR_1R_2-$ group between the boron atom and the cyano function (CN) is believed to provide a "damping effect" on electron withdrawal by the cyano group on the boron atom in the comparison to the cyanotrihydroborates where the boron atom is directly attached to the cyano moiety. As a result, the insertion of the $-CR_1R_2-$ group in organocyanohydroborates of the present invention helps to provide compounds which are intermediate in their capability to deliver a hydride ion.

The reactivity of the hydrogens attached to the boron atom can be further altered through the careful selection of an appropriate R group for both $R_1$ and $R_2$ in the compounds of the present invention. Thus, by varying the chemical species of $R_1$ and $R_2$, compounds having a variety of intermediate reducing capabilities can be provided in accordance with the present invention which have hereto been unknown. Moreover, since the reactivity and selectivity of hydroborates as reducing agents are substantially influenced by both steric and electronic considerations, careful selection of an appropriate chemical species for $R_1$ and $R_2$ provides reducing agents which are chemically selective in their reducing function.

Further, in this regard, it is possible to form a chiral carbon center around the $-CR_1R_2-$ moiety of the organocyanohydroborate compounds of the present invention through the proper choice of chemical species for $R_1$ and $R_2$. It is anticipated that such chirality may be significant in the stereo-selective reduction of organic functional groups and in providing starting materials for the synthesis of chiral cyanoboranes.

Thus, it will be appreciated that one of the important features of the present invention is the provision of cyanohydroborate compounds wherein a carbon atom is interposed between the boron atom and the cyano group so as to isolate the hydrogen atoms associated with the boron atom from the cyano group and thereby provide reducing agents with an intermediate reducing capacity. The interposition of this carbon atom with associated substituent groups is the reason these new compounds have been termed "organocyanohydroborates."

Following are several examples of organocyanohydroborate compounds which are made in accordance with the present invention. It will be understood that the following examples are given by way of example only, and are not to be considered as comprehensive of all of the compounds which can be produced in accordance with the present invention.

EXAMPLE 1

In this example, an organocyanohydroborate compound was made in accordance with the present invention wherein $R_1$ was represented by hydrogen (H), $R_2$ was represented by hydrogen (H), and $M^+$ was represented by lithium (LiL+) in Formulas 2A and 2B. Hence, the organocryanohydroborate compound made in this example has the following formula:

$LiBH_3CH_2CN$

In this example, all reagents and solvents were prepurified in the following manner. Tetrahydrofuran (THF) was refluxed over and distilled from cuprous chloride (CuCl) and then stored over solid potassium hydroxide (KOH) pellets. The THF was then redistilled from sodium metal and stored over 4A molecular sieves under a nitrogen atmosphere. Acetonitrile ($CH_3CN$) was refluxed over and distilled from calcium hydride ($CaH_2$) and stored over 4A molecular sieves under a nitrogen atmosphere. A 10.1 molar solution of n-butyllithium in hexane was used as purchased from the Aldrich Chemical Company, Milwaukee, Wis. Additionally, a 1.0 molar solution of $BH_3$ in THF solvent was also used as purchased from the Aldrich Chemical Company.

Further in this example, all glassware used was dried at about 120° C. overnight, assembled while hot, and then cooled under a nitrogen atmosphere. Further, all reagents and solvents employed in this example were transferred via syringe.

In Example 1, a dry ice-isopropanol slush was prepared having a temperature of about −78° C. A first 100 milliliter round bottom flask was immersed into the cold slush bath and was flushed with dry nitrogen gas. Subsequently, about 40 milliliters of THF solvent were added to the flask, followed by about 2.5 milliliters of the 10.1 molar n-butyllithium reagent and about 3.4 milliliters of the acetonitrile reagent. This mixture was magnetically stirred for approximately one hour.

During the one-hour stirring period, a second 250 milliliter round bottom flask was flushed with nitrogen gas and cooled to about −78° C. in a dry ice-isopropanol slush bath. About 40 milliliters of THF solvent and about 10 milliliters of the 1.0 molar $BH_3$ in THF solution were introduced into the second flask. At the conclusion of the one-hour mixing time for the first flask, the contents of the first flask were quantitatively transferred into the second flask containing the $BH_3$ in THF solution. This transfer was accomplished by connecting the two flasks via a double-tipped needle and using a positive pressure of nitrogen gas to force transfer from the first flask to the second flask. Following the transfer, the reaction mixture in the second flask was magnetically stirred for approximately one hour.

After stirring, the solvent in the second flask was evaporated off by heating the reaction mixture to about 40° C. under a reduced pressure of about 20 millimeters of mercury to yield a highly viscous oil. The identity of the $LiBH_3CH_2CN$ compound produced was supported by hydrogen-1 and boron-11 nuclear magnetic resonance (NMR) spectroscopy and infrared (IR) spectroscopy. The compound of this example has utility as a reducing agent for various organic functional groups.

EXAMPLE 2

In this example, an organocyanohydroborate compound was made in accordance with the present invention wherein $R_1$ was represented by hydrogen (H), $R_2$ was represented by a methyl group ($CH_3$), and $M^+$ was represented by lithium ($Li^+$) in Formulas 2A and 2B. Hence, the organocyanohydroborate compound made in this example has the following formula:

$LiBH_3CHCH_3CN$

This compound was made using a procedure similar to that for Example 1, with the following exceptions. Instead of the acetonitrile used in Example 1, about 7.9 milliliters of propionitrile ($CH_3CH_2CN$) were employed in the place thereof. Additionally, in Example 2, about 60 milliliters of THF solvent and about 4.2 milliliters of a 10.2 molar n-butyllithium reagent were added to the first flask with the propionitrile. In the second flask were mixed about 17 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 3

In this example, an organocyanohydroborate compound was made in accordance with the present invention wherein $R_1$ was represented by hydrogen (H), $R_2$ was represented by a phenyl group ($C_6H_5$), and $M^+$ was represented by lithium ($Li^+$) in Formulas 2A and 2B. Hence, the organocyanohydroborate compound made in this example has the following formula:

$LiBH_3CHC_6H_5CN$

This compound was made using a procedure similar to that for Example 1, with the following exceptions. Instead of the acetonitrile used in Example 1, about 15.7 milliliters of benzyl cyanide ($C_6H_5CH_2CN$, which was prepurified by distillation prior to use, and stored over 4A molecular sieves under an atmosphere of dry nitrogen gas) were employed in the place thereof. Additionally, in Example 3, about 60 milliliters of THF solvent and about 35.7 milliliters of a 1.4 molar n-butyllithium reagent were added to the first flask with the benzyl cyanide. In the second flask were mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 4

In this example, an organocyanohydroborate compound was made in accordance with the present invention wherein $R_1$ was represented by a methyl group ($CH_3$), $R_2$ was represented by a methyl group ($CH_3$), and $M^+$ was represented by lithium ($Li^+$) in Formulas 2A and 2B. Hence, the organocyanohydroborate compound made in this example has the following formula:

$LiBH_3C(CH_3)_2CN$

This compound was made using a procedure similar to that of Example 1, and was accomplished as follows. In Example 4, all reagents and solvents were prepurified in the following manner. Tetrahydrofuran (THF) was refluxed over and distilled from cuprous chloride (CuCl) and then stored over solid potassium hydroxide (KOH) pellets. The THF was then redistilled from sodium metal and stored over 4A molecular sieves under a nitrogen atmosphere. Isobutyronitrile (($CH_3)_2CHCN$) was refluxed over and distilled from calcium hydride ($CaH_2$) and stored over 4A molecular sieves under a nitrogen atmosphere. A 1.4 molar solution of n-butyllithium in hexane was used as purchased from the Aldrich Chemical Company. Additionally, a 1.0 molar solution of $BH_3$ in THF solvent was also used as purchased from the Aldrich Chemical Company.

Further in this example, all glassware used was dried at about 120° C. overnight, assembled while hot, and then cooled under a nitrogen atmosphere. Further, all reagents and solvents employed in this example were transferred via syringe.

In Example 4, a dry ice-isopropanol slush was prepared having a temperature of about −78° C. A first 250 milliliter round bottom flask was immersed into the cold slush bath and was flushed with dry nitrogen gas. Subsequently, about 60 milliliters of THF solvent were added to the flask, followed by about 30.3 milliliters of the 1.4 molar n-butyllithium reagent and about 10.0 milliliters of the isobutyronitrile reagent. This mixture was magnetically stirred for approximately one hour.

During the one-hour stirring period, a second 250 milliliter round bottom flask was flushed with nitrogen gas and cooled to about −78° C. in a dry ice-isopropanol slush bath. About 60 milliliters of THF solvent and about 17 milliliters of the 1.0 molar $BH_3$ in THF solution were introduced into the second flask. At the conclusion of the one-hour mixing time for the first flask, the contents of the first flask were quantitatively transferred into the second flask containing the $BH_3$ in THF solution. This transfer was accomplished by connecting the two flasks via a double-tipped needle and using a positive pressure of nitrogen gas to force transfer from the first flask to the second flask. Following the transfer, the reaction mixture in the second flask was magnetically stirred for approximately thirty minutes.

After stirring, the solvent in the second flask was evaporated off by heating the reaction mixture to about 40° C. under a reduced pressure of about 20 millimeters of mercury to yield a highly viscous oil. The identity of the LiBH$_3$C(CH$_3$)$_2$CN compound produced was verified using boron-11 nuclear magnetic resonance spectrometry. The compound of this example has utility as a reducing agent for various organic functional groups.

EXAMPLE 5

In this example, an organocyanohydroborate compound may be made in accordance with the present invention wherein R$_1$ is represented by a methyl group (CH$_3$), R$_2$ is represented by a phenyl group (C$_6$H$_5$), and M$^+$ is represented by lithium (Li$^+$) in Formulas 2A and 2B. Hence, the organocyanohydroborate compound of this example has the following formula:

LiBH$_3$CCH$_3$C$_6$H$_5$CN

This compound may be made using a procedure similar to that for Example 1, with the following exceptions. Instead of the acetonitrile used in Example 1, about 17.3 milliliters of alpha-methylphenylacetonitrile (CH$_3$CHC$_6$H$_5$CN) are employed in the place thereof. Additionally, in Example 5, about 60 milliliters of THF solvent and about 4.8 milliliters of a 10.5 molar n-butyllithium reagent are added to the first flask with the alpha-methylphenylaceonitrile. In the second flask are mixed about 20 milliliters of a 1.0 molar BH$_3$ in THF solution and about 60 milliliters of THF solvent in accordance with the procedure of Example 1. The compound of this example has utility as a reducing agent for various organic functional groups.

EXAMPLE 6

In this example, an organocyanohydroborate compound was made in accordance with the present invention wherein R$_1$ was represented by a phenyl group (C$_6$H$_5$), R$_2$ was represented by a phenyl group (C$_6$H$_5$), and M$^+$ was represented by lithium (Li$^+$) in Formulas 2A and 2B. Hence, the organocyanohydroborate compound made in this example has the following formula:

LiBH$_3$C(C$_6$H$_5$)$_2$CN

This compound was made using a procedure similar to that for Example 1, with the following exceptions. Instead of the acetonitrile used in Example 1, about 21.3 grams of diphenylacetonitrile (((C$_6$H$_5$)$_2$CHCN), predissolved in about 20 milliliters of THF) were employed in the place thereof. Additionally, in Example 6, about 60 milliliters of THF solvent and about 4.1 milliliters of a 10.5 molar n-butyllithium reagent were added to the first flask with the diphenyl-acetonitrile. In the second flask were mixed about 17 milliliters of a 1.0 molar BH$_3$ in THF solution and about 60 milliliters of THF solvent in accordance with the procedure of Example 1. The compound of this example has utility as a reducing agent for various organic functional groups.

EXAMPLE 7

In this example, an organocyanohydroborate compound was prepared in accordance with the present invention wherein R$_1$ and R$_2$ of Formulas 2A and 2B were both represented by a pentamethylene group (C$_5$H$_{10}$) connected to the alpha carbon at both ends thereof so as to form a cyclohexane ring with that carbon, and wherein M$^+$ was represented by lithium (Li$^+$).

Hence, the organocyanohydroborate compound made in this example had the following formula:

LiBH$_3$C(CH$_2$)$_5$CN

This compound was made using a procedure similar to that for Example 1, with the following exceptions. Cyclohexylcarbonitrile (C$_6$H$_{11}$CN) was purchased from Aldrich Chemical Company and used without further purification. The amounts of the various reactants used are as follows.

Into the first flask were introduced about 30 milliliters of the THF solvent, about 2.0 milliliters of a 10.2 molar n-butyllithium reagent, and about 6.2 milliliters of the cyclohexylcarbonitrile reagent in accordance with the procedure of Example 1. Into the second flask were introduced about 30 milliliters of THF solvent and about 8 milliliters of a 1.0 molar BH$_3$ in THF solution in accordance with the procedure of Example 1. The compound of this example has utility as a reducing agent for various organic functional groups.

EXAMPLES 8-14

In Examples 8-14 and 13-14, the dioxane adducts of each of the compounds made in Examples 1-4 and 6-7, respectively, were produced. In each of Examples 8-11 and 13-14, the 1,4-dioxane was prepurified by distillation from sodium metal, and stored over 4A molecular sieves under an atmosphere of dry nitrogen gas. Further, in each of Examples 8-11 and 13-14, a small quantity of the organocyanohydroborate compound from each of Examples 1-4 and 6-7, respectively, was mixed with enough 1,4-dioxane to totally dissolve the compound. It was found that about 35 milliliters of the 1,4-dioxane was adequate to dissolve about 17 millimoles of the organocyanohydroborate compound. This solution was then allowed to stand for a period of about 45 minutes to about one hour, during which time a white precipitate formed. The white precipitate was then removed by a vacuum filtration onto a glass fiber filter disc. In Example 12, the dioxane adduct of the compound of Example 5 is made by following the above-outlined procedure for Examples 8-11 and 13-14.

The compounds of these examples have utility as reducing agents for various organic functional groups. By way of example only, the compound produced in Example 18 has been found to effectively reduce benzaldehyde. However, its reduction utility is not limited to this one particular compound.

EXAMPLES 15-21

In Examples 15 and 17-18, organocyanohydroborate compounds were made in accordance with the present invention incorporating a tetraphenylphosphonium cation ((C$_6$H$_5$)$_4$P$^+$).

The reaction procedure was performed in an aqueous medium according to the following Equation IX:

Li$^+$BH$_3$CR$_1$R$_2$CN$^-$.X dioxane +       EQUATION IX (C$_6$H$_5$)$_4$P$^+$Br$^-$ $\xrightarrow{H_2O}$ (C$_6$H$_5$)$_4$P$^+$BH$_3$CR$_1$R$_2$CN$^-$ This reaction procedure was performed as follows. Chloroform solvent was purified by distillation from anhydrous calcium chloride (CaCl$_2$) and stored over 4A molecular sieves under a nitrogen atmosphere. In each of Examples 15 and 17-18, a small quantity of the dioxane adduct of the organocyanohydroborate compound from each of Examples 8 and 10–11, respectively, was added to enough distilled water to dissolve it. Subsequently, a saturated solution of tetraphenylphosphonium bromide (($C_6H_5$)$_4$P$^+$Br$^-$) was added dropwise until the thick white precipitate which appeared was completely formed. At this point, the precipitate was isolated by filtration, and the product was purified by dissolving it in purified chloroform, removing undissolved residue by filtration, and evaporating the chloroform off under vacuum. In each of Examples 16 and 19–21, the tetraphenylphosphonium salt of each of the compounds of Examples 9 and 12–14, respectively, is made by following the above-outlined procedure for Examples 15 and 17–18. The compounds of these examples have utility as reducing agents for various organic functional groups.

EXAMPLE 22

In this example, the reducing capacity of the organocyanohydroborate compound of Example 15, namely, ($C_6H_5$)$_4$P$^+$BH$_3$CH$_2$CN$^-$, was treated with respect to various organic ketones, aldehydes, and acids. It was observed that this particular organocyanohydroborate salt does indeed demonstrate chemo-selective reducing characteristics.

In Example 22, all qualitative reduction reactions were carried out in a five millimeter quartz NMR tube at ambient temperature, the NMR tube having been previously oven-dried. About 50 milligrams of the ($C_6H_5$)$_4$P$^+$BH$_3$CH$_2$CN$^-$ were added to the NMR tube along with about 50 milligrams of one of the following unsaturated organic reagents: benzophenone, acetophenone, 2-heptanone, benzaldehyde, heptaldehyde, benzoic acid, and heptanoic acid. About 0.5 milliliters of CDCl$_3$ solvent (previously dried over molecular sieves) were then added to the NMR tube.

The reaction products were analyzed using hydrogen-1 and boron-11 NMR spectroscopy. The results of these experiments are tabulated in Table I below.

TABLE I

| COMPOUND | Reduction to Alcohol? |
|---|---|
| Ketones | |
| Benzophenone | No |
| Acetophenone | No |
| 2-Heptanone | No |
| Aldehydes | |
| Benzaldehyde | Yes |
| Heptaldehyde | Yes |
| Acids | |
| Benzoic Acid | Yes |
| Heptanoic Acid | No |

As seen in Table I, chemo-selectivity of reduction of the various compounds tested was observed. For example, it is noted that the organocyanohydroborate compound used in this example, ($C_6H_5$)$_4$P$^+$BH$_3$CH$_2$CN$^-$, served to easily reduce each of the aldehydes tested to alcohols, while none of the ketones tested were reduced to alcohols. Additionally, reduction of the aromatic acid, benzoic acid was observed, but no reduction of the aliphatic acid, heptanoic acid, was observed.

It is particularly noteworthy that such chemoselectivity in providing for reduction of aldehydes and not ketones under such mild conditions is not typically observed using prior art reducing agents such as the borohydrides or cyanotrihydroborates. Hence, the results of Example 22 strongly suggest that the insertion of the —CR$_1$R$_2$— moiety between the BH$_3$ and CN moieties of the compounds of the present invention does indeed affect the reactivity of the hydrogens attached to the boron atom. Again, it should be reiterated that the reactivity of the boron hydrogens in the compounds of the present invention may be further altered by changing the substituent groups, R$_1$ and R$_2$, or by varying the cation in the particular organocyanohydroborate compound concerned.

EXAMPLE 23

In this example, a deuterated hydroborate compound (LiBH$_3$CD$_2$CN) may be made in accordance with the present invention. In this example, a procedure similar to that of Example 1 is followed, with the exception that deuterated acetonitrile-d$_3$ (CD$_3$CN) obtained, for example, from Aldrich Chemical Company, is used instead of the regular acetonitrile employed in Example 1. All amounts of the various reactants and reaction parameters in this example are identical to those used in Example 1. The compound of this example has utility as a reducing agent for various organic functional groups.

EXAMPLE 24

In this example, a deuterated hydroborate compound (LiBD$_3$2CH$_2$CN) was made in accordance with the present invention. In this example, a procedure similar to that of Example 1 was followed, with the exception that 1.4 molar deuterated borane-d$_3$(BD$_3$) in THF obtained from Alfa Products, Denvers, Mass., was used instead of the BH$_3$ in THF employed in Example 1. Further, in this example, about 25 milliliters of THF solvent, about 1.22 milliliters of 10.2 molar n-butyllithium and aobut 1.7 milliliters of acetonitrile reagent were added to the first flask according to the procedure of Example 1. In the second flask were mixed about 25 milliliters of THF solvent and about 3.6 milliliters of the 1.4 molar BD$_3$ in THF reagent according to the procedure of Example 1. The compound of this example has utility as a reducing agent for various organic functional groups, particularly with respect to its interaction with prochiral centers.

EXAMPLE 25

In this example, an organocyanohydroborate compound within the scope of the present invention may be made wherein R$_1$ is represented by hydrogen (H), R$_2$ is represented by an ethyl group (CH$_2$CH$_3$) and M$^+$ is represented by lithium (Li$^+$) in Formulas 2A and 2B. Hence, the organocyanohydroborate compound of this example has the following formula:

LiBH$_3$CHC$_2$H$_5$CN

This compound is made using a procedure similar to that for Example 1, with the following exceptions. Instead of the acetonitrile used in Example 1, about 11.3 milliliters of butyronitrile (CH$_3$CH$_2$CH$_2$CN) are employed in the place thereof. Additionally, in Example 25, about 60 milliliters of THF solvent and about 4.8 milliliters of a 10.5 molar n-butyllithium reagent are added to the first flask with the butyronitrile. In the second flask are mixed about 20 milliliters of a 1.0 molar BH$_3$ in THF solution and about 60 milliliters of THF solvent in accordance with the procedure of Example 1. The compound of this example has utility as a reducing agent for various organic functional groups.

EXAMPLE 26

This compound is made using a procedure similar to that for Example 1, with the following exceptions. Instead of the acetonitrile used in Example 1, about 13.6 milliliters of valeronitrile ($CH_3(CH_2)_3CN$) are employed in the place thereof. Additionally, in Example 26, about 60 milliliters of THF solvent and about 4.8 milliliters of a 10.5 molar n-butyllithium reagent are added to the first flask with the valeronitrile. In the second flask are mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 27

This compound is made using a procedure similar to that for Example 1, with the following exceptions. Instead of the acetonitrile used in Example 1, about 15.6 milliliters of hexanenitrile ($CH_3(CH_2)_4CN$) are employed in the place thereof. Additionally, in Example 27, about 60 milliliters of THF solvent and about 4.8 milliliters of a 10.5 molar n-butyllithium reagent are added to the first flask with the hexanenitrile. In the second flask are mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 28

This compound is made using a procedure similar to that for Example 1, with the following exceptions. Instead of the acetonitrile used in Example 1, about 20.0 milliliters of heptyl cyanide ($CH_3(CH_2)_6CN$) are employed in the place thereof. Additionally, in Example 28, about 60 milliliters of THF solvent and about 4.8 milliliters of a 10.5 molar n-butyllithium reagent are added to the first flask with the heptyl cyanide. In the second flask are mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 29

This compound is made using a procedure similar to that for Example 1, with the following exceptions. Instead of the acetonitrile used in Example 1, about 13.7 milliliters of 2-methylbutyronitrile ($CH_3CH_2CH(CH_3)CN$) are employed in the place thereof. Additionally, in Example 29, about 60 milliliters of THF solvent and about 4.8 milliliters of a 10.5 molar n-butyllithium reagent are added to the first flask with the 2-methylbutyronitrile. In the second flask are mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 30

This compound is made using a procedure similar to that for Example 1, with the following exceptions. Instead of the acetonitrile used in Example 1, about 8.6 grams of malononitrile ($CH_2(CN)_2$) dissolved in about 20 milliliters of THF are employed in the place thereof. Additionally, in Example 30, about 60 milliliters of THF solvent and about 4.8 milliliters of a 10.5 molar n-butyllithium reagent are added to the first flask with the malononitrile solution. In the second flask are mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 31

This compound is made using a procedure similar to that for Example 1, with the following exceptions. Instead of the acetonitrile used in Example 1, about 17.8 milliliters of heptanoic acid nitrile ($CH_3(CH_2)_5CN$) are employed in the place thereof. Additionally, in Example 31, about 60 milliliters of THF solvent and about 4.8 milliliters of a 10.5 molar n-butyllithium reagent are added to the first flask with the heptanoic acid nitrile. In the second flask are mixed about 20 milliliters of a 1.0 molar $BH_3$ in THF solution and about 60 milliliters of THF solvent in accordance with the procedure of Example 1. The compound of this example has utility as a reducing agent for various organic functional groups.

EXAMPLE 32

In this example, an amine-organocyanoborane compound was prepared in accordance with the present invention. In Example 32, a compound was prepared in accordance with Formula 4 with $R_1$ represented as hydrogen (H), $R_2$ represented as a phenyl group ($C_6H_5$), and with $R_3$, $R_4$, and $R_5$ all being methyl groups ($CH_3$). Hence, in this example, the compound produced had the following formula:

$(CH_3)_3NBH_2CHC_6H_5CN$

In this example, all glassware used was dried at about 120° C. overnight, assembled while hot, and then cooled under a nitrogen atmosphere. Further, all reagents and solvents employed in this example were transferred via syringe. The tetrahydrofuran (THF) used in this example was dried by refluxing the THF over $LiAlH_4$ and distilling the THF from the $LiAlH_4$. The THF was then stored over 4A molecular sieves under a nitrogen atmosphere.

In Example 32, dry ice-acetone slushes having a temperature of about $-78°$ C. were placed into two separate recrystallization dishes. Each recrystallization dish was in turn placed on top of a magnetic stirrer. Two 500 milliliter round bottom flasks (hereinafter referred to as flasks A and B) were fitted with stoppers and a magnetic stirring bar was placed into each flask. Flask A was then placed inside the $-78°$ C. slush within one of the recrystallization dishes, while flask B was placed into the $-78°$ C. slush within the second recrystallization dish.

Subsequently, about 60 milliliters of the dry THF were injected into flask A, followed by about 10 milliliters of a 10.1 molar solution of n-butyllithium in hexane and about 25 milliliters of a 12.8 molar solution of pure phenylacetylnitrile ($C_6H_5CH_2CN$). The resulting tan-colored solution was stirred in the $-78°$ C. bath for about one hour.

After stirring, about 50 milliliters of the dry THF were injected into flask B, followed by about 50 milliliters of 1.0 molar $BH_3$ in THF. The contents of flask A were then transferred to flask B via a double-tipped needle using positive nitrogen gas (N₂) pressure. The resultant mixture was stirred at about −78° C. for about 30 minutes.

Subsequently, a solution of (CH₃)₃NHCl in THF was prepared by mixing about 14.3 grams of the (CH₃)₃NHCl in about 175 milliliters of THF. The 175 milliliters of the resultant solution were then injected gradually into the contents of flask B at about −78° C. The resulting solution was then allowed to warm to ambient temperature, and flask B was then fitted with a reflux condenser. The solution was then refluxed under a nitrogen atmosphere for about 22 hours.

After refluxing, the solution was filtered to remove lithium chloride (LiCl). The filtrate was then concentrated by rotary evaporation to yield an oily white material. This material was washed with about 50 milliliters of (C₂H₅)₂O, and the (C₂H₅)₂O was then decanted off. This procedure was repeated three times and the resulting white powder (about a 9.88 gram yield) was sublimed at about 80° C. to yield relatively pure (CH₃)₃NBH₂CHC₆H₅CN.

The identity of the compound produced was supported by hydrogen-1 and boron-11 nuclear magnetic resonance (NMR) spectroscopy, infrared (IR) spectroscopy, and elemental analysis. The compound of this example has utility as a reducing agent for various organic functional groups.

EXAMPLE 33

In this example, an amine-organocyanoborane compound may be prepared in accordance with the present invention. In Example 33, a compound is prepared in accordance with Formula 4 with R₁ represented as a methyl group (CH₃), R₂ represented as a methyl group (CH₃), and with R₃, R₄, and R₅ all being methyl groups (CH₃). Hence, in this example, the compound produced has the following formula:

(CH₃)₃NBH₂C(CH₃)₂CN

In this example, all glassware used is dried at about 120° C. overnight, assembled while hot, and cooled under a nitrogen atmosphere. The tetrahydrofuran (THF) used in this example is prepurified and predried over solid potassium hydroxide (KOH) pellets and subsequently distilled from sodium metal.

In Example 33, the dioxane adduct of LiBH₃C(CH₃)₂CN from Example 11 is dried in vacuo prior to use. About 1.83 grams of the LiBH₃C(CH₃)₂CN dioxane, about 1.87 grams of trimethylamine hydrochloride (CH₃)₃NHCl, and about 100 milliliters of THF solvent are mixed together in a 500 milliliter round bottom flask. The mixture is stirred and heated to about 65° C., and is refluxed for about 25 hours. After refluxing, the solution is cooled and filtered to remove lithium chloride (LiCl). The solvent is then evaporated from the mixture using a water-aspirator vacuum having a pressure of about 20 millimeters of mercury. The resulting residual powder is then dried in vacuo. The compound of this example has utility as a reducing agent for various organic functional groups.

EXAMPLE 34

In this example, an amine-organocyanoborane compound may be prepared in accordance with the present invention. In Example 34, a compound is prepared in accordance with Formula 4 with R₁ represented as hydrogen (H), R₂ represented as hydrogen (H), and with R₃, R₄ and R₅ all being methyl groups (CH₃). Hence, in this example, the compound produced has the following formula:

(CH₃)₃NBH₂CH₂CN

The compound of this example is made using a procedure similar to that outlined above for Example 33 with the following exceptions. In Example 34, the dioxane adduct of LiBH₃CH₂CN from Example 8 is employed instead of the dioxane adduct used in Example 33. In this example, about 2.66 grams of the LiBH₃CH₂CN dioxane, about 8.12 grams of (CH₃)₃NHCl, and about 150 milliliters of THF are combined in accordance with the procedure of Example 33 with the exception that the mixture is refluxed for 18 hours. The compound of this example has utility as a reducing agent for various organic functional groups.

In summary, it will be appreciated that the present invention provides for a new class of cyanohydroborate compounds which are relatively easy to make and to purify. Additionally, by providing a class of cyanohydroborate compounds having a —CR₁R₂— moiety between the BH₃ moiety and the CN moiety, a class of hydroborate reducing agents having a very broad range of reducing capacity is provided. Indeed, the carbon atom interposed between the BH₃ moiety and CN moiety provides a "starting point" for producing a virtually limitless number of new reducing agents in accordance with the present invention.

It will be appreciated that the compounds and methods of the present invention are capable of being incorporated into a variety of embodiments, only a few of which have been illustrated and described above. Thus, the present invention may be embodied in other specific forms without departing from its spirit or essential characteristics. The described embodiments are to be considered only as illustrative and not restrictive, and the scope of the invention is, therefore, indicated by the appended claims rather than the foregoing description. All changes which came within the meaning and range of equivalency of the claims are to be embraced within their scope.

What is claimed and desired to be secured by U.S. Letters Patents is:

1. A chemical compound having the formula:

R₅R₄R₃NBH₂CR₁R₂CN wherein R₁ is selected from the group consisting of H, deuterium, CH₃ and C₆H₅;

wherein R₂ is selected from the group consisting of H, deuterium, CH₃, and C₆H₅; or wherein R₁ and R₂ are jointly represented as C₅H₁₀ so as to form a cyclohexyl ring with the alpha carbon of the compound;

wherein R₃ is selected from the group consisting of H, deuterium, CH₃, and C₆H₅;

wherein R₄ is selected from the group consisting of H, deuterium, CH₃, and C₆H₅; and wherein R₅ is selected from the group consisting of H, deuterium, CH₃, and C₆H₅.

2. A chemical compound as defined in claim 1 wherein R₃, R₄, and R₅ are all CH₃.

3. A chemical compound as defined in claim 1 wherein R₁ and R₂ are both H.

4. A chemical compound as defined in claim 1 wherein R₁ and R₂ are both CH₃.

5. A chemical compound as defined in claim 1 wherein $R_1$ is H and $R_2$ is $C_6H_5$.

6. A chemical compound as defined in claim 2 wherein $R_1$ is H and $R_2$ is H.

7. A chemical compound as defined in claim 2 wherein $R_1$ is $CH_3$ and $R_2$ is $CH_3$.

8. A chemical compound as defined in claim 2 wherein $R_1$ is H and $R_2$ is $C_6H_5$.

9. A chemical compound as defined in claim 1 wherein one or more of the hydrogen atoms attached to the boron atom is a deuterium atom.

10. A chemical compound as defined in claim 1 wherein $R_1$ and $R_2$ are both deuterium.

11. A chemical compound as deined in claim 1 wherein $R_1$ is H and $R_2$ is $CH_3$.

* * * * *

UNITED STATES PATENT AND TRADEMARK OFFICE
CERTIFICATE OF CORRECTION

PATENT NO. : 4,774,354

DATED : September 27, 1988

INVENTOR(S) : Morse et al.

It is certified that error appears in the above-identified patent and that said Letters Patent is hereby corrected as shown below:

Column 4, line 16, "M$^{30}$" should be --M$^+$--
Column 4, line 68, "about about" should be --about--
Column 5, line 30, "in tandem," should be --in tandem;--
Column 9, lines 33-34, "trailkylhydroborates" should be --trialkylhydroborates--
Column 9, line 50, "in the comparison" should be --in comparison--
Column 10, line 35, "(LiL$^+$)" should be --(Li$^+$)--

Column 15, line 22, "was treated" should be --was tested--
Column 16, line 31, "Denvers" should be --Danvers--
Column 22, line 6, "deined" should be --defined--

Signed and Sealed this

Eighteenth Day of July, 1989

Attest:

DONALD J. QUIGG

Attesting Officer

Commissioner of Patents and Trademarks